United States Patent [19]

Pilipski

[11] 4,235,968

[45] Nov. 25, 1980

[54] SACCHARIFICATION OF CELLULOSE

[75] Inventor: Mark Pilipski, 89 Mountainside Ter., Clifton, N.J. 07013

[73] Assignees: Mark Pilipski, Clifton, N.J.; Martin F. Sturman, Melrose Park, Pa.; Michael Ebert, Mamaroneck, N.Y.

[21] Appl. No.: 936,646

[22] Filed: Aug. 24, 1978

[51] Int. Cl.$^2$ .................. C13K 1/02; C12C 11/00
[52] U.S. Cl. ................................ 435/161; 127/37
[58] Field of Search ........................... 127/37; 435/161

[56] References Cited

U.S. PATENT DOCUMENTS

| | | | |
|---|---|---|---|
| 1,864,838 | 6/1932 | Langwell | 435/161 X |
| 2,289,808 | 7/1942 | Severson | 435/161 |
| 2,481,263 | 9/1949 | Tsuchiya | 435/161 X |
| 2,778,751 | 1/1957 | Riehm | 127/37 |
| 2,951,775 | 9/1960 | Apel | 127/37 |
| 3,391,135 | 7/1968 | Ouno | 127/37 X |

*Primary Examiner*—Sidney Marantz
*Attorney, Agent, or Firm*—Michael Ebert

[57] ABSTRACT

A method for effecting saccharification of raw cellulosic material taken from any available source. In the first step, the raw material is immersed in a caustic solution which swells the cellular structure to render it more reactive and acts to solubilize the lignins and other compounds contained therein, these being washed away to provide a prepared cellulosic material. In the second step, the prepared material is subjected to a viscose process to produce a viscous solution of sodium cellulose xanthate in sodium hydroxide, from which solution the aqueous phase is separated to provide a viscose intermediate. In the final step, the viscose intermediate is hydrolyzed by immersing it in a bath of anhydrous liquid hydrogen chloride to yield usable glucose and other products.

8 Claims, No Drawings

SACCHARIFICATION OF CELLULOSE

BACKGROUND OF INVENTION

This invention relates generally to a method to effect saccharification of cellulosic material, and more particularly to a method for the production of ethyl alcohol or ethanol from cellulosic waste material saccharified by liquefied hydrogen chloride.

The hydrolysis of cellulose yields a mixture of simple reducing sugars, mainly glucose. These hydrolysis products are convertible by fermentation to ethyl alcohol which can be used as a liquid fuel to replace gasoline. In terms of available energy, expressed either as the heat of combustion of cellulose or of the glucose or alcohol theoretically obtainable therefrom, a pound of cellulose is equivalent to 0.35 lb. of gasoline.

Billions of tons of carbon are fixed every year on the land area of the earth by photosynthesis, out of which about half appears in the form of cellulose. The sheer magnitude of this potential source and the fact that petroleum-derived fuels are becoming increasingly scarce and more expensive, has awakened great interest in the exploitation of otherwise unused waste cellulosic materials.

About two hundred ninety million tons per year of residual, institutional and commercial solid wastes containing approximately fifty percent paper and other cellulosic materials are generated in the United States. Moreover, about sixty million tons of bagasse are available. These altogether contain about one hundred and twenty million tons of usable cellulose, the energy equivalence of which is nearly a fifth of the current U.S. gasoline consumption. Furthermore, 2.3 billion tons per year of agricultural wastes in the United States having a high cellulose content, increase this supply significantly. Despite these many and varied sources of available cellulose, a major industrial alcohol fermentation process can only be successful if the reducing sugars can be derived from a cellulosic material at a sufficiently low price.

Early efforts in this direction were mainly geared to the acid hydrolysis of wood products to sugars. In recent years, various methods have been proposed to carry out cellulose degradation through enzymatic means. Thus U.S. Pat. Nos. 3,642,580; 3,764,475 and 4,009,075 effect the conversion of cellulose to simple sugars by enzymatic hydrolysis, the resultant sugars then being fermented by yeasts to produce alcohol.

Hydrolysis is a chemical reaction in which water reacts with a compound to cause the decomposition or splitting thereof. Water in the form of its hydrogen and hydroxyl ions adds to the cleaved compound. Hydrolysis is generally catalyzed by ions. In the absence of ions, hydrolysis may be a very slow process. Thus the use of an acid as a catalyst increases the concentration of hydrogen or hydroxyl ions with a corresponding rise in the rate of hydrolysis. The hydrolysis of some organic compounds is also catalyzed by certain enzymes.

It is known that the polysaccharide components of wood and other cellulosic materials can be partially or completely hydrolyzed by acid catalyzed reactions in which the cellulose is converted to glucose and the hemicellulose mostly to xylose. The resultant syrupy mixture or molasses of wood sugar may be used as cattle feed, or it may be fermented to alcohol. Alternatively, the glucose derived in this manner may be separated from the wood sugars and purified.

Cellulose is a D-glucose polymer with $\beta$ (1-4) linkages. Related compounds are polymers of D-xylose with $\beta$ (1-4) linkages and side chains of arabinose and other sugars. The glycosidic bonds between these various sugar sub-units —O— are akin to ether bonds, acetal bonds and hemiacetal bonds, which bonds are hydrolyzable by acids. An aqueous acid not only acts as a catalyst for these reactions, but also supplies water thereto. This characteristic of an aqueous acid gives rise to a major drawback in the hydrolysis of cellulose.

When, for example, cellulosic material is treated with an aqueous solution of hydrogen chloride (hydrochloric acid) as a catalyst promoting hydrolysis, those cellulose molecules having exposed glucose sub-units will be hydrolyzed. But the free glucose resulting from this process is hydroscopic in nature and renders the remaining cellulose inaccessible to chemical decomposition. The same problem arises with the enzymatic hydrolysis of cellulose.

As a consequence, existing processes using aqueous acids or enzymes to catalyze the decomposition of cellulosic compounds by hydrolysis give a poor yield or are very energy consumptive. This renders such processes uneconomic and impractical when, for example, the controlling consideration is the comparative cost of conventional fuels and an equivalent amount in terms of energy content of ethyl alcohol produced by saccharification and fermentation.

SUMMARY OF INVENTION

The main object of this invention is to provide an efficient and economic process for the saccharification of cellulosic material giving a high yield.

While the glucose resulting from a process in accordance with the invention may be fermented to produce ethyl alcohol that is directly useful as a fuel or in an admixture with gasoline to provide a low-cost fuel having a high energy content, the ethyl alcohol derived from cellulosic waste is also valuable as a solvent, an extractant, an intermediate in the synthesis of various organic chemicals or as essential ingredients in many pharmaceuticals.

Also an object of the invention is to provide a method which extracts not only glucose from cellulosic material but many useful byproducts, so that virtually all components of the cellulosic stock are extracted in an exploitable form.

Briefly stated, in a saccharification method in accordance with the invention, raw cellulosic material from any available source is first subjected to steeping in a caustic solution, causing the cellular structure of the raw stock to swell to render it more reactive. Lignins and other components present in the matrix are solubilized by the solution and then washed away so that the cellulosic material is now in the prepared state.

In the next step, the prepared cellulosic material is subjected to viscose processing in which it is treated with carbon disulfide to produce a viscous solution of sodium xanthate in aqueous sodium hydroxide. The aqueous phase is separated from the residue, a viscose intermediate.

In the final step, the viscose intermediate is subjected in a pressurized chamber maintained at a temperature level appropriate to an anhydrous liquid hydrogen chloride bath to hydrolysis, the intermediate being immersed in the bath and being converted thereby into glucose and other reducing substances.

Because this process eliminates the high percentage of water included in prior techniques using aqueous acids as catalysts or enzyme solutions, the yield of free sub-units is increased to a substantial degree beyond that heretofore attainable. And because the reaction is highly exothermic and energetic, and water in bulk is not present, many intermediate compounds are formed which are exploitable.

DESCRIPTION OF INVENTION

The method in accordance with the invention is applicable to any cellulosic source such as waste wood, pulp, paper, hay, fallen leaves, bagasse, sawdust or any finely-divided plant wastes as well as the effluents from paper and pulp processing, such as the Kraft or sulfite processes. It is also applicable to municipal wastes, in which case the waste slurry, after being dewatered in a filter press, is constituted by a mass having a total solids content largely composed of cellulosic materials.

The products derived from the method may vary in their relative proportions, depending on the nature of the starting cellulose source. By way of illustration, we shall apply the method in accordance with the invention to wood sawdust. Accordingly, the basic nature of this wood will first be considered.

All wood substances are composed of two chemical materials: lignin and a polysaccharidic system which is termed "holocellulose." Holocellulose is composed of cellulose and hemicelluloses, a mixture of pentosans, hexosans and polyuronides, and in some cases, small amounts of pectic material.

In a wood cell, the outer portion of the primary wall is heavily lignified and the intercellular substance is also mainly lignin, the lignin serving as a matrix in which the cellulosic cells are embedded. Dissolution and removal of the lignin therefore results in separation of the wood fibers.

In addition to the cell wall tissue, which is the fundamental material of all wood substance, wood contains a variety of other materials which are extractable by selected solvents. These extraneous components lie mainly within the cavities of the cells and the surfaces of the cell walls, and include aliphatic hydrocarbons, resin acids, dyes and proteins. Generally, however, the total amount of the extraneous components is only a few percent of the total wood weight.

Step I (Steeping)

The sawdust (or other raw cellulosic material to be processed) is first immersed in a caustic solution such as sodium or potassium hydroxide to effect mercerization thereof. Usable for this purpose is a 17 to 20 percent solution of sodium hydroxide at a temperature of between 18° to 25° C.

During this treatment, the hydroxyl groups of the cellulose reacts with sodium hydroxide to form alkali cellulose. However, the primary function of this steeping step is to increase the reactivity of cellulose to subsequent processing by swelling the fibers thereof and also to render the lignins and other compounds present in the cellulose matrix soluble.

The sawdust so treated is then washed with steam, solvents or water, or combinations thereof, to remove therefrom the ligneous substances and other aromatic, polar and nonpolar soluble substances such as rosin. The removed compounds are usable commercially as solvents, varnishes, glues, paint constituents, cleaning compounds, etc., and they therefore represent valuable byproducts of the process. What remains after these compounds are removed is a prepared cellulosic material.

Step 2 (Viscose Processing)

Viscose is the industrial term for a viscous solution of sodium cellulose xanthate in an aqueous sodium hydroxide, the solution having an orange-red color. The principal raw materials for the viscose processing are cellulose, sodium hydroxide, carbon disulfide and water. Industrial processes based on viscose are widely used for the manufacture of rayon and cellulose film or cellophane.

In the second step, the prepared cellulose material derived from step one is viscose-processed in the manner described in U.S. Pat. Nos. 2,855,321 and 2,985,674, or in accordance with any other known viscose process.

Upon completion of viscose processing, the aqueous phase is separated from the solution, leaving a viscose intermediate which is ready to be treated in step three. The liquid so removed is useful as a byproduct for the production of rayon, cellophane and related products.

Step 3 (Hydrolysis)

In this final step, the viscose intermediate derived from step 2 is hydrolyzed by immersing it in a bath of anhydrous liquid hydrogen chloride. Since this cryogenic liquid must be maintained under pressure at a relatively low temperature so that it remains below its boiling point, this step is carried out in a pressurized chamber under relatively low temperature conditions, bearing in mind the known relationship between vapor pressure and temperature for hydrogen chloride in its liquid and gaseous phases, as set forth in the Matheson Gas Data Book (page 2).

Because hydrolysis with anhydrous liquid hydrogen chloride eliminates the bulk of water accompanying hydrolysis of cellulose by aqueous acid, the yield of free sub-units is much higher than has heretofore been obtainable. The products resulting from the reaction with anhydrous liquid hydrogen chloride starting with raw sawdust are many useful reducing substances, including glucose, galactose, pentoses, homogentisic acid, ascorbic acid, paraldehyde and lactose.

The sugars and carbohydrates generated by a method in accordance with the invention may be used directly as foodstuffs or livestock feed, as well as the starting material for ethyl alcohol production by known fermentation techniques. The salient advantage of the present method over prior techniques is that its useful yield is much higher; for it makes full utilization of virtually all components present in the raw cellulosic stock. Thus the method is economically feasible to produce ethyl alcohol as a fuel competitive with existing petroleum-derived fuels.

While there has been described a preferred technique for saccharification of cellulose in accordance with the invention, it will be appreciated that many changes and modifications may be made therein without, however, departing from the essential spirit thereof.

I claim:

1. A method to effect saccharification of raw cellulosic material taken from any available source, comprising the steps of:
    A. steeping the raw material in a caustic solution to swell the cellular structure of the material to render it more reactive and to solubilize the lignins and other compounds contained therein;

B. washing away the solubilized lignins and other compounds to provide a prepared cellulosic material;

C. subjecting the prepared material to viscose processing to produce a viscous solution of sodium cellulose xanthate in aqueous sodium hydroxide;

D. removing the aqueous phase of the viscous solution to provide a viscose residue intermediate; and E. hydrolyzing the viscose intermediate by immersing it in a bath of anhydrous liquid hydrogen chloride to yield a usable glucose and other products.

2. A method as set forth in claim 1, wherein said cellulosic material is sawdust.

3. A method as set forth in claim 1, wherein said caustic solution is sodium hydroxide.

4. A method as set forth in claim 1, wherein said caustic solution is potassium hydroxide.

5. A method as set forth in claim 1, wherein said washing is effected by a solvent.

6. A method as set forth in claim 1, wherein said viscose processing subjects said prepared material to carbon disulfide.

7. A method as set forth in claim 1, wherein said intermediate is hydrolyzed in a pressure chamber which is maintained at a low temperature to prevent boiling of said liquid hydrogen chloride.

8. A method as set forth in claim 1, further including the step of fermenting the glucose to produce ethyl alcohol.

* * * * *